(12) United States Patent
Haas et al.

(10) Patent No.: US 7,981,391 B2
(45) Date of Patent: Jul. 19, 2011

(54) AQUEOUS HYDROGEN PEROXIDE SOLUTIONS AND METHOD OF MAKING SAME

(75) Inventors: Thomas Haas, Frankfurt (DE); Claudia Brasse, Hanau (DE); Guido Stochniol, Gelnhausen (DE); Jürgen Glenneberg, Offenbach (DE); Wolfgang Wöll, Maintal-Dörnigheim (DE)

(73) Assignee: Evonik Degussa GmbH, Essen (DE)

( * ) Notice: Subject to any disclaimer, the term of this patent is extended or adjusted under 35 U.S.C. 154(b) by 151 days.

(21) Appl. No.: 12/541,674

(22) Filed: Aug. 14, 2009

(65) Prior Publication Data

US 2009/0294727 A1    Dec. 3, 2009

Related U.S. Application Data

(62) Division of application No. 10/669,978, filed on Sep. 24, 2003, now Pat. No. 7,722,847.

(60) Provisional application No. 60/414,327, filed on Sep. 30, 2002.

(51) Int. Cl.
*C01B 15/023* (2006.01)
*C01B 15/037* (2006.01)

(52) U.S. Cl. .................. 423/272; 423/273; 423/588

(58) Field of Classification Search .................. 423/272, 423/273, 588, 584, 589, 590
See application file for complete search history.

(56) References Cited

U.S. PATENT DOCUMENTS

| | | | |
|---|---|---|---|
| 2,624,655 A | 1/1953 | Greenspan | |
| 2,870,171 A | 1/1959 | Gable | |
| 3,761,580 A | 9/1973 | Schreyer et al. | |
| 3,912,766 A | 10/1975 | Logan et al. | |
| 3,949,063 A | 4/1976 | Coingt et al. | |
| 4,410,501 A | 10/1983 | Taramasso et al. | |
| 4,485,084 A | 11/1984 | McIntyre | |
| 4,503,028 A | 3/1985 | Franzén et al. | |
| 4,534,945 A | 8/1985 | Hopkins et al. | |
| 4,606,905 A | 8/1986 | Thirion | |
| 4,812,173 A | 3/1989 | Tsao et al. | |
| 4,833,260 A | 5/1989 | Neri et al. | |
| 4,889,689 A | 12/1989 | Tsao | |
| 4,981,662 A | 1/1991 | Dougherty | |
| 4,999,179 A | 3/1991 | Sugihara et al. | |
| 5,200,166 A | 4/1993 | Shiga et al. | |
| 5,232,680 A | 8/1993 | Honig et al. | |
| 5,302,367 A | 4/1994 | Signorini et al. | |
| 5,523,426 A | 6/1996 | Jubin, Jr. et al. | |
| 5,591,875 A | 1/1997 | Chang et al. | |
| 5,599,955 A | 2/1997 | Vora et al. | |
| 5,620,935 A | 4/1997 | Thiele | |
| 5,675,026 A | 10/1997 | Thiele | |
| 5,760,253 A | 6/1998 | Danner et al. | |
| 5,849,937 A | 12/1998 | Jubin, Jr. et al. | |
| 5,849,938 A | 12/1998 | Rueter et al. | |
| 5,912,367 A | 6/1999 | Chang | |
| 6,013,237 A | 1/2000 | Kajiwara et al. | |
| 6,042,807 A | 3/2000 | Faraj | |
| 6,054,109 A | 4/2000 | Saito et al. | |
| 6,063,941 A | 5/2000 | Gilbeau | |
| 6,296,829 B1 | 10/2001 | Devos et al. | |
| 6,300,506 B1 | 10/2001 | Paparatto et al. | |
| 6,333,018 B2 | 12/2001 | Bianchi et al. | |
| 6,372,924 B2 | 4/2002 | Thiele | |
| 6,429,322 B1 | 8/2002 | Catinat et al. | |
| 6,592,840 B1 | 7/2003 | Fischer et al. | |
| 6,780,206 B2 | 8/2004 | Nordhoff et al. | |
| 6,815,552 B2 | 11/2004 | Strebelle et al. | |
| 6,896,867 B2 | 5/2005 | Tanaka et al. | |
| 6,939,527 B2 | 9/2005 | Oeter et al. | |
| 7,320,779 B2 | 1/2008 | Strebelle et al. | |
| 2003/0162983 A1 | 8/2003 | Strebelle et al. | |

FOREIGN PATENT DOCUMENTS

| | | |
|---|---|---|
| DE | 977 130 | 3/1965 |
| DE | 1 945 750 | 1/1971 |
| DE | 196 23 611 | 12/1997 |
| DE | 197 23 950 | 12/1998 |
| DE | 197 54 185 | 2/1999 |
| DE | 198 35 907 | 2/2000 |
| DE | 198 36 547 | 2/2001 |
| DE | 100 28 363 | 11/2001 |
| EP | 0 032 338 | 7/1981 |
| EP | 0 100 118 | 2/1984 |
| EP | 0 100 119 | 2/1984 |
| EP | 0 133 510 | 2/1985 |
| EP | 0 230 349 | 7/1987 |
| EP | 0 230 949 | 8/1987 |

(Continued)

OTHER PUBLICATIONS

Gook, G. et al., "Ulimann's Encyclopedia of Industrial Chemistry, Fifth Edition," 1989, pp. 447-457, vol. A 13, XP-002233848, VCH Verlasgesellschaft, Weinheim, Germany (11 pages).

(Continued)

*Primary Examiner* — Wayne Langel
(74) *Attorney, Agent, or Firm* — Smith, Gambrell & Russell, LLP

(57) ABSTRACT

An aqueous hydrogen peroxide solution containing i) less than 50 wppm alkali metals, alkaline earth metals or combinations thereof in total, irrespective whether the alkali or alkaline earth metals are present in cationic or complex form; ii) less than 50 wppm of amines having a $pk_B$ of less than 4.5 or the corresponding protonated compounds in total; and iii) at least 100 wppm anions or compounds that can dissociate to form anions in total, where the wppm are based on the weight of hydrogen peroxide and the concentration of hydrogen peroxide is more than 50% by weight based on the total weight of the hydrogen peroxide solution. A process for preparation of said hydrogen peroxide solution and the use of said solution in a process for epoxidation of olefins is also disclosed.

14 Claims, No Drawings

FOREIGN PATENT DOCUMENTS

| | | |
|---|---|---|
| EP | 0 425 893 | 5/1991 |
| EP | 0 426 949 | 5/1991 |
| EP | 0 568 336 | 11/1993 |
| EP | 0 568 337 | 11/1993 |
| EP | 0 583 828 | 2/1994 |
| EP | 0 645 473 | 3/1995 |
| EP | 0 659 473 | 6/1995 |
| EP | 0 712 852 | 5/1996 |
| EP | 0 719 768 | 7/1996 |
| EP | 0 757 043 | 2/1997 |
| EP | 0 757 045 | 2/1997 |
| EP | 0 795 537 | 9/1997 |
| EP | 0 827 765 | 3/1998 |
| EP | 0 930 308 | 7/1999 |
| EP | 0 936 219 | 8/1999 |
| EP | 0 940 393 | 9/1999 |
| EP | 1 072 599 | 1/2001 |
| EP | 1 072 600 | 1/2001 |
| EP | 1 122 248 | 8/2001 |
| EP | 1 138 387 | 10/2001 |
| EP | 1 167 290 | 1/2002 |
| EP | 1 221 442 | 7/2002 |
| FR | 2 810 981 | 1/2002 |
| GB | 811733 | 4/1959 |
| JP | 59-51273 | 3/1984 |
| JP | 2166636 | 6/1990 |
| JP | 8-143303 | 6/1996 |
| JP | 8-225556 | 9/1996 |
| JP | 9-118671 | 5/1997 |
| JP | 11-139811 | 5/1999 |
| JP | 11-292521 | 10/1999 |
| JP | 2000-302419 | 10/2000 |
| WO | WO 97/47613 | 12/1997 |
| WO | WO 97/47614 | 12/1997 |
| WO | WO 98/47845 | 10/1998 |
| WO | WO 99/01445 | 1/1999 |
| WO | WO 99/07690 | 2/1999 |
| WO | WO 99/11639 | 3/1999 |
| WO | WO 00/07695 | 2/2000 |
| WO | WO 00/17178 | 3/2000 |
| WO | WO 00/25881 | 5/2000 |
| WO | WO 00/76989 | 12/2000 |
| WO | 01/34301 | 5/2001 |
| WO | 01/57012 | 8/2001 |
| WO | WO 01/57012 | 8/2001 |
| WO | 01/92149 | 12/2001 |
| WO | WO 01/92242 | 12/2001 |
| WO | WO 02/02545 | 1/2002 |

OTHER PUBLICATIONS

European Search Report, dated Mar. 26, 2003, issued by the European Patent Office for European Patent Application No. EP 02021967.1 (4 pages).

Bellinger et al., "Chemical Propellants, Corrosion and Stability Studies", Industrial and Engineering Chemistry, Mar. 1946 vol. 38, No. 3, pp. 310-320.

Kirk-Othmer, "Encyclopedia of Chemical Technology", Fourth Edition, vol. 20, 1996, p. 287.

"Ullmann's Encyclopedia of Industrial Chemistry", Fifth, Completely Revised Edition, Ed. Elvers et al., vol. A13, pp. 443-457, 1989.

Solvay Chemical, "High Purity Grade Hydrogen Peroxide" created Oct. 20, 2003, modified Mar. 18, 2004.

"Handbook of Chemistry and Physics", $79^{th}$ edition, Ed. Lide, 1998-1999, pp. 8-44-8-51, CRC press.

Huber et al., "Quantification and Characterization of Organic Impurities in Semiconductor-Grade Hydrogen Peroxide with a Direct Chromatographic Method", Semiconductor Pure Water and Chemicals Conference, 1997, $16^{th}$(vol. 2), pp. 15-30, Publisher Balazs Analytical Laborator.

Kovacevic et al., "Determination of bisphosphonates by ion chromatography-inductively coupled plasma mass spectrometry", Journal of Chromatography A, 1039, 2004, pp. 77-82.

Semi C30-1101, Specifications and Guideline for Hydrogen Peroxide, Sep. 2001 pp. 1-12.

Fang, "Overview on Reaction Carriers and Solvent Components for the Production of Hydrogen Peroxide by Anthraquinone Process", English translation , Chinese Journal of Science & Technology in Chemical Industry, 1998, 6(3):18-23.

Weissermel et al., "Industrielle Organische Chemie", 3. überarbeitete und erweiterte Auflage, 1988, S. 348-351.

Collard et al., "Implementing enhanced ICP-MS technology to attain Semi Grade 5 purity levels", Micro, Jan. 2002.

S.J. Weterback, A.E. Martell, Ethylene-diamine-tetra(methylenephosphonic) Acid, Nature, 1956, 178, pp. 321-322.

N.F. Hall et al., The Journal of the American Chemical Society, Sep. 1932, vol. 54, No. 9, pp. 3469-3483.

K.T. Leffek et al., Basicity of substituted 2-phenyl-1,1,1,1-tetramethyguanidines and others bases in acetonitrile solvent,Journal of Chemistry, 1989, vol. 67, pp. 590-595.

John W. Bunting et al. "Equilibration of N-(2-Cyanoethyl)pyridinium Cations with Substituted Pyridines and Acrylonitrile. A Change in Rate-Determining Step in an E1cb Reaction", Journal of the American Chemical Society, 1990, 112, pp. 8878-8885.

AQUEOUS HYDROGEN PEROXIDE SOLUTIONS AND METHOD OF MAKING SAME

This application is a divisional of our U.S. patent application Ser. No. 10/669,978, filed Sep. 24, 2003 now U.S. Pat. No. 7,722,847, which is relied on and incorporated herein by reference. U.S. patent application Ser. No. 10/669,978 claims the benefit of U.S. patent application Ser. No. 60/414,327, filed Sep. 30, 2002, expired.

INTRODUCTION

The present invention relates to specific aqueous hydrogen peroxide solutions that are characterized by a maximum amount of alkali metals, alkaline earth metals, and amines having a $pk_B$ of less than 4.5, and that are particularly suitable for use in processes for the epoxidation of olefins. In another aspect, the present invention relates to a process for the preparation of such an aqueous hydrogen peroxide solution.

BACKGROUND OF THE INVENTION

Today, the vast majority of hydrogen peroxide is produced by the well-known anthraquinone process. A survey of the anthraquinone process and its numerous modifications is given in G. Goor, J. Glenneberg, S. Jacobi: "Hydrogen Peroxide" Ullmann's Encyclopedia of Industrial Chemistry, Electronic Release, $6^{th}$ ed. Wiley-VCH, Weinheim June 2000, page 14. Generally, the anthraquinone loop process comprises the following steps:

(a) Hydrogenation of a working solution comprising an organic solvent or mixture of organic solvents, and one or more active anthraquinone compounds;

(b) oxidation of the resulting hydrogenated working solution to form hydrogen peroxide;

(c) extraction of hydrogen peroxide with water;

(d) stabilizing of the extracted aqueous hydrogen peroxide solution;

(e) drying of the working solution after extraction; and (f) regeneration and purification of the working solution.

For each of the above distinct process steps, the Ullmann reference discloses numerous different possibilities.

Crude hydrogen peroxide solutions or concentrated hydrogen peroxide solutions obtained from the anthraquinone process contain a plurality of compounds in addition to hydrogen peroxide in low concentrations. These compounds are either impurities or additives like stabilizers. The impurities are compounds that are extracted from the working solution into the aqueous phase. They are mainly ionic or polar species like carboxylic acids, alcohols, carbonyl compounds and amines. These impurities are therefore also found in commercial hydrogen peroxide solutions.

For example, hydroquinone solvents that are commonly used in the above described process are nitrogen containing compounds like amides and ureas (see Ullmann supra page 6). Particularly preferred are tetraalkyl ureas like tetrabutyl urea. The use of these solvents result in amine impurities like monoalkyl or dialkyl, especially monobutyl and dibutyl, amines in the final hydrogen peroxide solutions. For example, the commercial hydrogen peroxide solution HYPROX® available from Degussa AG contains up to 200 wppm mono- and dibutyl amine based on the weight of hydrogen peroxide.

Depending on the final use of the hydrogen peroxide solutions, it is also known to conduct additional purification steps in order to obtain the required specification for the respective use of the hydrogen peroxide solution.

For example, DE-A 100 26 363 discloses a purification process for aqueous hydrogen peroxide solutions, whereby the solutions are treated with an anion exchange resin, a nonionic absorbing resin having a specific structure, and a neutral absorbing resin also having a specific macroporous structure. The hydrogen peroxide solutions obtained in this way are substantially free of cationic, anionic and organic impurities. Therefore, the solutions are particularly useful in microelectronics applications.

Similarly U.S. Pat. No. 4,999,179 discloses a process for purification of hydrogen peroxide solutions that contain, after purification, each metal cation in an amount of less than 5 ppb, each anion in an amount of less than 10 ppb and organic impurities in an amount of not more than 5 ppm in terms of total organic carbon content.

The drawback of such methods is that the purification is extremely expensive and can therefore, for economic reasons, not be used for the preparation of chemical mass products like propylene oxide. Furthermore, such highly purified hydrogen peroxide solutions are substantially free of anionic components like phosphates and nitrates that are necessary for the stabilization of aqueous—especially highly concentrated—hydrogen peroxide solutions for safety reasons.

From EP-A 100 119, it is known that propene can be converted by hydrogen peroxide into propene oxide if a titanium-containing zeolite is used as catalyst.

Since then, many investigations with respect to the effect of the addition of basic, acidic and ionic compounds either during preparation of the titanium silicalite catalyst or their presence in the reaction mixture on the activity and selectivity of the catalysts have been published.

From EP-A 230 949, it is known to neutralize the titanium silicalite catalyst either prior to its use in an epoxidation reaction or in situ with strong bases thereby introducing large amounts of alkali metal or alkaline earth metal ions into the reaction mixture. Said neutralization resulted in an increase in activity and selectivity to the desired olefin oxide in a batch process.

The experiments in EP-A 757 043, however, show that in a continuous process the activity is considerably reduced if the catalyst is neutralized prior to or during the reaction. Therefore, it is suggested to treat the catalyst prior to or during the epoxidation reaction with a neutral or acidic salt. The experimental data in EP-A 757 043 confirm that by addition of neutral or acidic salts the selectivity is increased but the activity is less reduced compared to the addition of a base. But EP-A 757 043 only shows examples wherein the catalyst is treated with the salt prior to the reaction and the catalyst is used in slurry form. Additionally, the experiments were only run for 8 hours but nevertheless show a dramatic drop in catalyst activity only after 4 hours, which is by no means acceptable for an industrial process.

Similarly, EP-A 712 852 teaches that by performing an epoxidation process catalyzed by titanium silicalite in the presence of a non-basic salt the selectivity is increased. All the examples are run in batch operation mode with a stirred catalyst slurry for one hour. Although it can be confirmed that the presence of non-basic salts may have a positive influence on catalyst selectivity in a short term experiment, it was discovered that even if non-basic salts are present in a reaction mixture for a continuous epoxidation reaction the activity and selectivity drops dramatically over time. Thus, the teaching of EP-A 712 852 does not lead to a reaction system that can be economically employed in a continuous epoxidation process using hydrogen peroxide in the presence of a heterogeneous catalyst.

In WO 00/76989, the influence of ionic components in commercially available aqueous hydrogen peroxide solutions that are used in epoxidation reactions as described in the above prior art documents is discussed. Ionic components, especially phosphates and nitrates, are added to commercially available aqueous hydrogen peroxide solutions as stabilizers to reduce hazardous decomposition of hydrogen peroxide. Contrary to the disclosure in the above prior art documents, WO 00/76989 teaches that the presence of ionic components in the reaction mixture—even those that have been added as stabilizers to commercial hydrogen peroxide—is detrimental to the long term selectivity in a continuous titanium silicalite catalyzed epoxidation reaction and should therefore be reduced to a minimum.

Contrary to the above prior art documents, continuous reactions running up to 300 hours were conducted showing that if ionic components are present in an amount of more than 100 ppm the long term selectivity is reduced. To solve this problem, it is suggested to remove ionic components from hydrogen peroxide solutions prior to use in epoxidation reactions by means of ion exchangers. Moreover, WO 00/76989 teaches that ammonium compounds and ammonia should be avoided under any circumstances since these compounds may lead to undesired side products by oxirane ring opening reactions with the formed olefin oxide. Although the teaching in WO 00/76989 leads to some improvement in long term selectivity compared to the above art, this improvement is still insufficient for an industrial scale process. Furthermore, this improvement can only be achieved with the complicated and, both in terms of investment and process costs, economically undesirable additional process step of ion exchange. Last but not least, removal of stabilizing ions like phosphate and nitrate from the hydrogen peroxide solution makes the process more hazardous and additional measures have to be taken to ensure safety during the entire process.

Contradicting the teaching of WO 00/76989, WO 01/57012 discloses that the use of crude hydrogen peroxide solutions directly obtained from the anthraquinone process having large amounts of, for example, sodium, nitrate, phosphate, and organic impurities, is superior with respect to product selectivity compared to highly purified hydrogen peroxide solutions containing very low amounts of sodium, nitrate, and phosphate. The experiments, however, were only conducted for a few hours so that the long term activity and selectivity of the catalyst cannot be determined from that reference.

Again another approach is disclosed in WO 01/92242, wherein a titanium silicalite catalyzed process for epoxidation of olefins using crude hydrogen peroxide solutions in the presence of a compound having aminocarbonyl functionality in which the nitrogen bears at least one hydrogen atom is disclosed. The examples show a batch type process that is conducted up to a conversion of hydrogen peroxide of 85%. After two hours the reaction is terminated even if the conversion of 85% has not been reached. Although the experimental data show an improvement with respect to the reaction rate compared to compounds with aminocarbonyl functionality having no hydrogen atom bonded to the nitrogen atom, long term activity and selectivity of the catalyst in a continuous process is not determinable from the information in WO 01/92242.

DE-A 199 36 547 discloses a continuous titanium silicalite catalyzed process for epoxidation of olefins with hydrogen peroxide whereby the conversion is kept constant by increase of reaction temperature and adjusting the pH of the reaction mixture. In a long term experiment (1000 hours), it could be verified that by adjusting the pH the increase in temperature and the rate of increase could be reduced compared to an experiment without pH adjustment. But conversion and selectivity were the same, irrespective of whether the pH was adjusted or not.

Thus, the object of the present invention is to provide an aqueous hydrogen peroxide solution that can be economically produced, that can be safely handled, stored, and shipped, and that is suitable for the epoxidation of olefin in the presence of a heterogeneous catalyst and leads to improved long term activity and selectivity of the catalyst.

SUMMARY OF THE INVENTION

In carrying out the present invention there is prepared an aqueous hydrogen peroxide solution comprising:
  i) less than 50 wppm of a member selected from the group consisting of an alkali metal, an alkaline earth metal or combinations thereof in total, irrespective whether the alkali or alkaline earth metals are present in cationic or complex form;
  ii) less than 50 wppm of amines having a $pk_B$ of less than 4.5 or the corresponding protonated compounds in total; and
  iii) at least 100 wppm anions or compounds that can dissociate to form anions in total,
  whereby the wppm are based on the weight of hydrogen peroxide.

This inventive aqueous hydrogen peroxide solution can be obtained by a process for the preparation of the hydrogen peroxide solution according to the anthraquinone loop process comprising:
  (a) hydrogenation of a working solution comprising an organic solvent or mixture of organic solvents and one or more active anthraquinone compounds,
  (b) oxidation of the resulting hydrogenated working solution to form hydrogen peroxide,
  (c) extraction of hydrogen peroxide with water,
  (d) stabilizing of the resulting extracted aqueous hydrogen peroxide solution,
  (e) concentrating the aqueous hydrogen peroxide solution to a concentration of hydrogen peroxide of at least 50% by weight based on the weight of the hydrogen peroxide solution,
  (f) drying of the working solution after extraction, and
  (g) regeneration and purification of the working solution, and during the entire process neither alkali or alkaline earth metals nor amines having a $pk_B$ of less than 4.5 or compounds forming such amines during the process are introduced in amounts that result in amounts of
    i) 50 wppm or more of alkali metals, alkaline earth metals or combinations thereof in total, irrespective whether the alkali or alkaline earth metals are present in cationic or complex form; or
    ii) 50 wppm or more of amines having a $pk_B$ of less than 4.5 or the corresponding protonated compounds in total;
    in the resulting aqueous hydrogen peroxide solution, where the wppm are based on the weight of hydrogen peroxide.

The hydrogen peroxide solution of the present invention is particularly suitable for use in a process for the epoxidation of olefins in the presence of a heterogeneous catalyst. It is a surprising result of the present invention that a hydrogen peroxide solution fulfilling the above-specified requirements and that can be safely handled, stored, and shipped, can easily be prepared in an economical process. Furthermore, surprisingly, this aqueous hydrogen peroxide solution leads to an improved long term activity and selectivity of the heterogeneous catalyst in an epoxidation process. Consequently, the overall economics of an epoxidation process can be considerably improved using the inventive aqueous hydrogen peroxide solution, since the solution itself can be economically produced and leads to reduced deactivation of the catalyst so that the operation time between regeneration cycles in the epoxidation process can be increased.

DETAILED DESCRIPTION OF THE INVENTION

The present inventors have thus discovered, contrary to the teaching of the prior art, that the presence of alkali metals and alkaline earth metals above a certain limit are detrimental to the activity and selectivity of the catalyst employed in epoxidation reactions of olefins. Moreover, the inventors have recognized that—in addition to alkali metals and alkaline earth metals—amines having a $pk_B$ of less than 4.5 are even more detrimental to the activity and selectivity of the catalyst, and therefore their content in hydrogen peroxide solutions that are used in epoxidation reactions of olefins has to be carefully controlled to be below the specified limits. On the other hand, anions like phosphate or nitrates, that are frequently used to stabilize aqueous hydrogen peroxide solutions, have no or only very little effect on the activity and selectivity of the epoxidation catalyst. Since these anions are necessary for the stabilization in order to ensure safety of handling, storing, and shipping of the aqueous hydrogen peroxide solution, they should be present in stabilizing amounts of at least 100 wppm based on the weight of the hydrogen peroxide in the solution.

Contrary to the teaching of the prior art, neither the use of crude hydrogen peroxide solutions obtained from the anthraquinone process without carefully controlling the amount of alkali metals and amines having a $pk_B$ below 4.5, nor the use of purified hydrogen peroxide solutions, where in addition to the metal cations also the stabilizing anions have been removed, are suitable for an economical process for epoxidation of olefins.

Although an amount of alkali metals or alkaline earth metals of less than 50 wppm based on the weight of hydrogen peroxide in the solution is acceptable, it is preferred to reduce the amount of these components to be less than 40 wppm, more preferred less than 35 wppm, in order to further improve the long term activity and selectivity of the catalyst.

So far, in the literature, the detrimental effect on amines having a $pk_B$ of less than 4.5 on the long term selectivity and activity of an epoxidation catalyst has not been recognized.

The effect of the presence of such amines is even more pronounced than the effect of the alkali metals or alkaline earth metals. Therefore, it is particularly preferred to reduce the amount of amines having a $pk_B$ of less than 4.5 in the aqueous hydrogen peroxide solution in total to less than 40 wppm, preferably less than 30 wppm, more preferably less than 20 wppm, and most preferably less than 10 wppm, based on the weight of hydrogen peroxide in the solution.

Especially detrimental to the activity and selectivity of the epoxidation catalyst is the presence of alkyl amines, especially secondary and tertiary alkyl amines.

Another surprising result of the inventors' investigations is that although amines having a $pk_B$ below 4.5 above certain amounts dramatically reduce the long term activity and selectivity of the epoxidation catalyst, the addition of at least 100 wppm of bases having a $pk_B$ of at least 4.5 even improve the long term activity and selectivity of the epoxidation catalyst. Thus, according to a preferred embodiment of the present invention, the aqueous hydrogen peroxide solution contains in addition at least 100 wppm of bases having a $pk_B$ of at least 4.5, or the corresponding protonated compounds in total based on the weight of hydrogen peroxide.

These bases may be either introduced during the process for preparation of the hydrogen peroxide or may be added to the hydrogen peroxide solution at any stage between production of the solution and final use in the epoxidation reaction.

Such bases are preferably present in the hydrogen peroxide solution in an amount of at most 3000 wppm in total, more preferred from 150 to 2000 wppm, particularly preferred from 200 to 1500 wppm, and most preferred from 300 to 1200 wppm, based on the total weight of hydrogen peroxide.

Such bases are preferably selected from organic amines and amides having a $pk_B$ of at least 4.5, organic hydroxylamines having a $pk_B$ of at least 4.5, ammonia and hydroxylamine. Ammonia is particularly preferred.

It is a particular advantage of the hydrogen peroxide solutions of the present invention that anions can be present in the usual stabilizing amounts. These stabilizing anions are preferably any kind of oxophosphorous anions like orthophosphate, hydrogen phosphate, dihydrogen phosphate, pyrophosphate, nitrate.

These stabilizing anions, or compounds that can dissociate in the hydrogen peroxide solution to produce these stabilizing anions, are preferably present in an amount of at most 1000 wppm, preferably 100-1000 wppm, more preferred 200-800 wppm, most preferred 200-600 wppm, based on the weight of hydrogen peroxide.

Thus, the hydrogen peroxide solution of the present invention ensures high selectivity and activity of a catalyst in the epoxidation reaction without compromising safety when handling, storing, and shipping the hydrogen peroxide solution.

Another advantage of the hydrogen peroxide solution of the present invention is that it can be easily produced in an economical way employing the well-known anthraquinone process, whereby additional purification steps are not necessary and are preferably not carried out when conducting the process of the present invention. The only requirement for the process of the present invention compared to the known modifications of the anthraquinone process is that the process has to be carefully controlled to avoid introduction of alkali metals, alkaline earth metals, amines having a $pk_B$ of less than 4.5, or compounds that may form, during the anthraquinone process, such amines during the preparation of the hydrogen peroxide solution in amounts that would result in concentrations above the limits specified according to the present invention.

Although many variations of the anthraquinone process to achieve this requirement are conceivable, it is particularly preferred to use a working solution that is essentially free of organic nitrogen compounds, to dry the working solution in above step (f) without using alkali metals or alkaline earth metal compounds that are in the anthraquinone process of the prior art commonly employed for drying, and to regenerate the working solution in step (g) by treating with active aluminum oxide. Preferably, drying is conducted by water evaporation in vacuum.

Thus, the process of the present invention provides the inventive hydrogen peroxide solution that is particularly useful in epoxidation reactions without employing cost- and labor-intensive purification steps. It follows that a crude hydrogen peroxide solution obtained from the process of the present invention can be used directly without any further purification steps.

It is preferred to concentrate the hydrogen peroxide solution to a hydrogen peroxide concentration of more than 50% by weight, preferably more than 60% by weight, most preferred from 60 to 70% by weight, based on the total weight of the hydrogen peroxide solution. The inventors have recognized that such concentrated hydrogen peroxide solutions are particularly useful in the epoxidation reaction since they further improve the long term activity and selectivity of the catalyst.

The hydrogen peroxide solution of the present invention can be employed in any epoxidation reaction using hydrogen peroxide known in the art. It is particularly preferred to use the present hydrogen peroxide solution in a continuous epoxidation process conducted in the presence of a water-miscible solvent and a heterogeneous catalyst. Preferably, the solvent is methanol, the olefin is propene, and the heterogeneous catalyst is a titanium silicalite catalyst.

The invention will now be explained in more detail with reference to the following examples.

EXAMPLES

Example 1

Preparation of an aqueous hydrogen peroxide solution according to the present invention.

In a trial plant for the loop process according to the anthraquinone process for the preparation of hydrogen peroxide comprising the steps of hydrogenation, oxidation, extraction, drying, and regeneration, a working solution is used comprised of 0.11 mol/l 2-ethyl anthraquinone, 0.29 mol/l 2-ethyl tetra-hydroanthraquinone, 0.13 mol/l 2-isohexyl anthraquinone, and 0.12 mol/l 2-isohexyl tetra-hydroanthraquinone in a solvent mixture comprising 75 vol % of $C_9/C_{10}$ alkyl substituted aryl compounds, and 25 vol % of tris(2-ethyl hexyl) phosphate. In the hydrogenation step, a loop reactor was run at a hydrogen pressure of 0.35 MPa and a temperature of 58° C. Palladium black (0.5:1 g/l) was used as hydrogenation catalyst. The hydrogen peroxide equivalent in the hydrogenation was 13.0 g/l.

After the hydrogenation, a part of the hydrogenated working solution is regenerated using active aluminum oxide. Thereafter, the combined working solution is oxidized using the Laporte oxidation as described in Ullmann, supra, page 14. Thereafter, the hydrogen peroxide is extracted using deionized water. To the extraction water, 50 ppm $H_3PO_4$ and 20 ppm $HNO_3$, both based on the weight of the hydrogen peroxide were added. The concentration of the extracted aqueous hydrogen peroxide solution was 41%. The working solution was dried by water evaporation in vacuum, and thereafter recycled to the hydrogenation step. The crude hydrogen peroxide solution was stabilized using 200 ppm sodium pyrophosphate based on the weight of hydrogen peroxide and concentrated in vacuum by water evaporation.

The hydrogen peroxide concentration of the solution obtained in this way was 43 wt-%, based on the total weight of the solution, and contained 250 mg/kg $H_2O_2$ phosphates, 20 mg/kg $H_2O_2$ nitrate, and 30 mg/kg $H_2O_2$ of sodium.

Examples 2 to 5 and Comparative Examples 1 to 3

The hydrogen peroxide solution obtained from Example 1 is concentrated to a hydrogen peroxide concentration as indicated in Table 1.

Additionally, alkali metal ions and/or amines having a $pk_B$ of less than 4.5 are added as indicated in Table 1. Furthermore, ammonia is added in an amount of 500 wppm (1000 wppm ammonia in example 5), based on the weight of hydrogen peroxide.

A titanium silicalite catalyst was employed in all examples. The titanium silicalite powder was shaped into 2 mm-extrudates using a silica sol as binder in accordance with Example 5 in EP-A 1 183 387.

Epoxidation is carried out continuously in a reaction tube of 300 mm volume, a diameter of 10 mm, and a length of 4 m. The equipment further comprises three containers of liquids and relevant pumps and a liquid separation vessel. The three containers for liquids contained methanol, the hydrogen peroxide solution, and propene. The reaction temperature is controlled via an aqueous cooling liquid circulating in a cooling jacket, whereby the cooling liquid temperature is controlled by a thermostat. The reaction pressure was 27 bar absolute. Mass flow of the feeding pumps were adjusted to result in a propene concentration of 38 wt-%, a methanol feed concentration of 48.7 wt-%, and a hydrogen peroxide feed concentration of 8 wt-%. The reactor was operated in down-flow operation mode. The cooling jacket temperature was adjusted to 35° C. and total mass flow was 0.35 kg/h. Product output and propene oxide concentration were determined by gas chromatography, and the hydrogen peroxide conversion by titration. The selectivity of hydrogen peroxide with respect to propene oxide was calculated.

The results are given in Table 1.

TABLE 1

| Example | Addition [mg/kg $H_2O_2$] | $H_2O_2$ concentration [wt-%] | Running time [h] | $CH_2O_2$ [%] | $SH_2O_2$ to PO [%] |
|---|---|---|---|---|---|
| 2 | — | 60 | 649 | 95 | 91 |
| 3 | Na 25 | 70 | 754 | 95 | 90 |
| 4 | Li 25 | 60 | 988 | 94 | 89 |
| 5 | — | 60 | 2356 | 94 | 90 |
| C1 | Na 20; dibutyl amine 135 | 43 | 2083 | 26 | 72 |
| C2 | methyl amine 100 | 60 | 1193 | 22 | 81 |
| C3 | 170 | 60 | 1007 | 89 | 79 |

In Table 2, the $pk_B$ values for nitrogen-containing bases are given.

TABLE 2

| Bases | $pk_B$ |
|---|---|
| Ammonia | 4.76 |
| Methyl amine | 3.36 |
| Dibutyl amine | 2.75 |

As is evident from the experimental results summarized in Table 1, high hydrogen conversions and selectivities can be maintained for a long running time of the experiment if the alkali metal concentration is below 50 wppm, based on the weight of hydrogen peroxide. When looking to the comparative examples, it becomes evident that if the claimed limits for alkali metal ions and amines having a $pk_B$ below 4.5 are exceeded, the conversion as well as the selectivity of the catalyst dramatically drops over time.

Further variations and modifications of the foregoing will be apparent to those skilled in the art and are intended to be encompassed by the claims appended hereto.

The invention claimed is:
1. An aqueous hydrogen peroxide solution comprising:
(I) less than 50 wppm alkali metals, alkaline earth metals or combinations thereof in total, irrespective whether the alkali metals or alkaline earth metals are present in cationic or complex form;
(ii) less than 50 wppm of amines having a pkB of less than 4.5 or the corresponding protonated compounds in total;

(iii) at least 100 wppm anions or compounds that can dissociate to form anions in total; and the wppm being based on the weight of hydrogen peroxide; and (iv) at least 100 wppm of bases having a pkB of at least 4.5 or the corresponding protonated compounds in total based on the weight of hydrogen peroxide;

wherein the amount of components of group iv) in total is 3000 wppm at most, based on the total weight of hydrogen peroxide, said aqueous hydrogen peroxide solution having been prepared according to anthraquinone loop process.

2. The aqueous hydrogen peroxide solution of claim 1, wherein the amount of components of group i) in total is less than 40 wppm, based on the weight of hydrogen peroxide.

3. The aqueous hydrogen peroxide solution of claim 1, wherein the amount of components of group i) in total is less than 35 wppm, based on the weight of hydrogen peroxide.

4. The aqueous hydrogen peroxide solution of claim 1, wherein the amount of components of group ii) in total is less than 40 wppm based on the weight of hydrogen peroxide.

5. The aqueous hydrogen peroxide solution of claim 1, wherein the amount of components of group ii) in total is less than 30 wppm based on the weight of hydrogen peroxide.

6. The aqueous hydrogen peroxide solution of claim 1, wherein the amount of components of group ii) in total is less than 20 wppm based on the weight of hydrogen peroxide.

7. The aqueous hydrogen peroxide solution of claim 1, wherein the amount of components of group ii) in total is less than 10 wppm based on the weight of hydrogen peroxide.

8. The aqueous hydrogen peroxide solution of claim 1, wherein the amines are selected from the group consisting of primary, secondary and tertiary alkyl amines.

9. The aqueous hydrogen peroxide solution of claim 1, wherein the amount of components of group iv) in total is from 150 to 2000 wppm, based on the total weight of hydrogen peroxide.

10. The aqueous hydrogen peroxide solution of claim 1, wherein the amount of components of group iv) in total is from 200 to 1500 wppm, based on the total weight of hydrogen peroxide.

11. The aqueous hydrogen peroxide solution of claim 1, wherein the amount of components of group iv) in total is from 300 to 1200 wppm, based on the total weight of hydrogen peroxide.

12. The aqueous hydrogen peroxide solution of claim 1, wherein the bases of group iv) are selected from the group consisting of organic amines and amides having a pkB of at least 4.5, organic hydroxylamines having a pkB of at least 4.5, ammonia and hydroxylamine.

13. The aqueous hydrogen peroxide solution of claim 12, wherein the bases of group iv) is ammonia.

14. The aqueous hydrogen peroxide solution of claim 1 wherein the anthraquinone loop process comprises:

(a) hydrogenation of a working solution comprising an organic solvent or mixture of organic solvents and one or more active anthraquinone compounds, (b) oxidation of the resulting hydrogenated working solution to form hydrogen peroxide, (c) extraction of hydrogen peroxide with water, (d) stabilizing of the resulting extracted aqueous hydrogen peroxide solution, (e) concentrating the aqueous hydrogen peroxide solution to a concentration of hydrogen peroxide of at least 50% by weight based on the weight of the hydrogen peroxide solution, (f) drying of the working solution after extraction, and (g) regeneration and purification of the working solution, and during the entire process neither alkali or alkaline earth metals nor amines having a pkB of less than 4.5 or compounds forming such amines during the process are introduced in amounts that result in amounts of i) 50 wppm or more of alkali metals, alkaline earth metals or combinations thereof in total, irrespective whether the alkali or alkaline earth metals are present in cationic or complex form; or ii) 50 wppm or more of amines having a pkB of less than 4.5 or the corresponding protonated compounds in total;

in the resulting aqueous hydrogen peroxide solution, where the wppm are based on the weight of hydrogen peroxide.

* * * * *